(12) United States Patent
Holmes et al.

(10) Patent No.: US 9,234,906 B2
(45) Date of Patent: Jan. 12, 2016

(54) LOW CARRYOVER LIQUID HANDLING PROBE FOR AN AUTOMATED ANALYZER

(75) Inventors: Laura Elizabeth Schilling Holmes, Chaska, MN (US); Steve M. Alseth, Cologne, MN (US); John G. Carver, Delano, MN (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 14/129,382

(22) PCT Filed: Jun. 27, 2012

(86) PCT No.: PCT/US2012/044431
§ 371 (c)(1),
(2), (4) Date: Apr. 3, 2014

(87) PCT Pub. No.: WO2013/006343
PCT Pub. Date: Jan. 10, 2013

(65) Prior Publication Data
US 2014/0234169 A1    Aug. 21, 2014

Related U.S. Application Data

(60) Provisional application No. 61/504,070, filed on Jul. 1, 2011.

(51) Int. Cl.
*G01N 35/10* (2006.01)

(52) U.S. Cl.
CPC ........ *G01N 35/1065* (2013.01); *G01N 35/1011* (2013.01); *G01N 35/1016* (2013.01); *G01N 2035/1025* (2013.01)

(58) Field of Classification Search
CPC ................. B01L 3/02; G01N 35/1009; G01N 2035/1025
USPC .......................................................... 422/509
See application file for complete search history.

(56) References Cited

U.S. PATENT DOCUMENTS

| | | | |
|---|---|---|---|
| 4,276,260 A | 6/1981 | Drbal et al. | |
| 4,615,866 A * | 10/1986 | Hyde et al. | 422/106 |
| 5,133,392 A | 7/1992 | Hamann | |
| 5,443,791 A | 8/1995 | Cathcart et al. | |
| 5,550,059 A | 8/1996 | Boger et al. | |
| 5,639,426 A * | 6/1997 | Kerr et al. | 422/501 |
| 5,895,630 A | 4/1999 | Skaborn et al. | |
| 6,270,726 B1 | 8/2001 | Tyberg et al. | |
| 6,363,802 B1 | 4/2002 | Grippo et al. | |
| 6,551,558 B1 | 4/2003 | Mann et al. | |

(Continued)

FOREIGN PATENT DOCUMENTS

| | | |
|---|---|---|
| DE | 10 2009 049 783 A1 | 4/2011 |
| JP | 3-183958 A | 8/1991 |

OTHER PUBLICATIONS

DuPont Teflon PFA-C-980 Product Information, p. 2.*

(Continued)

*Primary Examiner* — Jill Warden
*Assistant Examiner* — Matthew Krcha
(74) *Attorney, Agent, or Firm* — Kilpatrick Townsend & Stockton LLP

(57) ABSTRACT

Provided herein is a carryover-reducing liquid handling probe for an analytical system, incorporating a rigid sheath and a polymer core that extends from the sheath to act as the fluid contact surface.

9 Claims, 2 Drawing Sheets

(56) References Cited

U.S. PATENT DOCUMENTS

| | | | |
|---|---|---|---|
| 7,144,554 | B1 | 12/2006 | Gulla et al. |
| 2003/0187600 | A1 | 10/2003 | Barnes |
| 2005/0019921 | A1 | 1/2005 | Orwar et al. |
| 2005/0054777 | A1* | 3/2005 | Lee .............................. 525/199 |
| 2006/0048570 | A1 | 3/2006 | Eglauer et al. |
| 2006/0115971 | A1 | 6/2006 | Bau et al. |
| 2007/0109139 | A1 | 5/2007 | Wenzig et al. |
| 2007/0264723 | A1 | 11/2007 | Kim et al. |
| 2008/0176292 | A1* | 7/2008 | Ugaz et al. .................. 435/91.2 |
| 2009/0226346 | A1 | 9/2009 | Miyato et al. |
| 2011/0125050 | A1 | 5/2011 | Bau et al. |
| 2013/0136672 | A1 | 5/2013 | Blumentritt et al. |

OTHER PUBLICATIONS

International Search Report and Written Opinion mailed on Oct. 29, 2012 for PCT Patent Application No. PCT/US2012/044431, 20 pages.

* cited by examiner

LOW CARRYOVER LIQUID HANDLING PROBE FOR AN AUTOMATED ANALYZER

CROSS REFERENCE TO RELATED APPLICATIONS

The present application is a US National Stage Entry under §371 of International Application No. PCT/US2012/044431, filed Jun. 27, 2012 which claims priority to U.S. Provisional Application No. 61/504,070, filed Jul. 1, 2011, the disclosures of which are incorporated by reference herein in their entirety for all purposes.

BACKGROUND

A wide variety of automated analyzers are available, performing analyses that range from simple pH determination to sophisticated testing that determines the presence of genetic markers. Despite this range of functions and capabilities, however, nearly all automated analyzers have common basic functionalities and performance issues. An automated analyzer must manipulate patient samples, which are generally liquids, such as blood, plasma, serum, urine, cerebrospinal fluid, or saliva. Solid or semisolid samples, such as tissue samples and fecal material, can treated as a liquid following maceration and suspension in a liquid. As such samples are provided in containers, such as venous blood collection tubes, and are generally manipulated by aspiration from these containers using one or more liquid handling probes. In order to move these fluids and liquid reagents to different locations on an automated analyzer a liquid handling probe may be attached to a moving carriage.

Automated analyzers generally share a common workflow, each step of which is a potential source of error that can degrade system performance. In a typical automated analyzer containers holding liquid samples are first loaded into the system by the operator. A robotic liquid handling probe then removes a portion of the sample which is used for testing. One or more reagents, which are also generally in liquid form, are retrieved from storage using a robotic liquid handling probe and subsequently mixed with the sample in order to perform an assay reaction that generates a detectable result.

As noted above liquid transfer is a process that is performed frequently on automated analyzers, and is a potential source of error that may degrade the quality of assay results. One assay characteristic that can be severely impacted by such errors is sensitivity, which is essentially a measure of the lowest concentration of a particular analyte that the analyzer can reliably detect or quantify. In many instances the sensitivity of a particular assay is a function of variation in the signal associated with a result from an assay performed on sample that does not contain the analyte, also known as the background signal. A large amount of variation in the background signal results will limit the sensitivity of the analyzer to concentrations of the analyte that return a relatively strong signal, one that is statistically distinguishable from the widely varying background signal. Conversely, a small amount of variation in the background signal can permit the detection of relatively low concentrations or analyte that generate a relatively weak signal.

One source of variation in the background signal is carryover or contamination. Carryover occurs when material is transferred from a first fluid to an analyzer component and then from that analyzer component to a second fluid. A typical scenario is when a small volume of fluid from a patient sample containing a very high concentration of analyte is transferred to a second patient sample by a liquid handling probe, leading to a falsely positive test result from the second sample. Similar transfers of liquid assay reagents are also possible.

Carryover can occur by physical transfer of a volume of fluid. This can occur in crevices that are inherent in the design of the liquid handling probe, or may take place in irregularities in the surface of the liquid handling probe that may occur due to rough handling or inadvertent collisions during use. Another source of carryover is the interaction of specific molecules in the sample with a wetted surface of the liquid handling probe. Once bound to such a surface these molecules may subsequently be released when the liquid handling probe enters a different fluid. Carryover may also occur by a combination of these mechanisms.

A number of approaches have been developed to minimize carryover. One of these is the use of disposable tips to handle fluids. These tips are applied to the liquid handling probe mechanism prior to handling a fluid and disposed of thereafter. Supplying and manipulating these disposable tips can add significant cost and complexity to an automated analyzer, and the time required to attach and dispose of the tips can impact system throughput. Improper attachment of a tip to a liquid handling probe may also lead to delivery of inaccurate volumes that impact assay results, and thereby become yet another source of variation.

Another approach is to implement rigorous washing procedures of the interior and exterior of the liquid handling probe mechanism. Numerous devices and methods for this have been disclosed, however these add significantly to the cost and complexity of an analyzer in the form of the need for additional workstations and wash reagents. In addition to impacting system throughput, these washing steps also are an additional source of variation in the analyzer.

Carryover of fluid volumes can be minimized without resorting to these measures by optimizing analyzer functions to reduce exposure of the liquid handling probe mechanism to the sample, for example by using liquid level sensing to detect the surface of the sample liquid and subsequently immerse only a small portion of the liquid handling probe. The liquid handling probe mechanism itself can be designed so as to present a surface without features that can trap liquids. This can be accomplished by electropolishing exposed metal surfaces and utilizing materials, such as stainless steel, that resist scratching. Positioning of the liquid handling probe can also be monitored to avoid collisions that may generate surface scratches and chips.

Carryover due to the binding of molecules to the material of the liquid handling probe can be avoided by selecting materials with a low tendency to interact with molecules in solution. These are typically polymers, such as polypropylene or fluoropolymers. A liquid handling probe may be constructed entirely of these materials, however the relative lack of strength and rigidity can complicate mounting such devices to motion systems and subsequent accurate positioning, particularly in a high throughput analyzer that may be making rapid movements. In addition, since such materials are generally nonconductive they are not compatible with many liquid level sensing mechanisms. Low nonspecific binding materials can be used as coatings over more conventional rigid materials, such as stainless steel. Such coatings are easily damaged through careless handling and accidental collision, however, generating surface scratches and chips in the polymer coating that can lead to significant fluid volume carryover.

Embodiments of the invention address these and other problems, individually and collectively.

SUMMARY

Provided herein is carryover-reducing liquid handling probe for an analytical system, incorporating a rigid sheath and a polymer core that extends from the sheath to act as the fluid contact surface. The polymer core can be conductive so that the extended portion can act as part of a liquid level sensor. The device may also include a shock absorbing mount that simplifies user replacement of the liquid handling probe and helps minimize damage during use. The shock absorbing mount can incorporate sensors that detect collisions, and signal the analytical system to take further steps that reduce damage to the liquid handling probe.

Provided herein is a liquid handling probe (or fluid handling probe) comprising an elongated rigid sheath with a distal (or lower) terminus; a conductive polymer core that is at least partially enclosed within said elongated rigid sheath, said conductive polymer core including an internal fluid conduit and a conductive polymer tip; and a liquid level sensing mechanism operably connected to the conductive polymer core. In some embodiments, said conductive polymer tip comprises a portion of the conductive polymer core that protrudes from the distal terminus of the elongated rigid sheath. In some embodiments, the conductive polymer core extends beyond the distal end of the elongated rigid sheath at least 0.05 inch, e.g., 0.1 inch, 0.25 inch, 0.5 inch, 0.75 inch, 1 inch, 0.05-2 inch, 0.1-1 inch, 0.1-0.5 inch, etc. In some embodiments, the elongated rigid sheath has a proximal (or upper) terminus. In some embodiments, the conductive polymer core protrudes from the proximal terminus to form a flared fitting.

In some embodiments, the elongated rigid sheath comprises stainless steel, e.g., electropolished stainless steel. In some embodiments, the elongated rigid sheath is conductive, and the conductive polymer core is in electrical contact with said elongated rigid sheath. In some embodiments, the fluid sensing mechanism is a capacitance based liquid sensing circuit. In some embodiments, the conductive polymer core comprises a conductive polymer with a bulk resistivity of less than $0.5\ \Omega\text{*m}$, e.g., 0.4, 0.3, 0.25, 0.1, 0.05, 0.1-0.5, or 0.2-0.4 $\Omega\text{*m}$. In some embodiments, the conductive polymer core comprises a conductive fluoropolymer. In some embodiments, the conductive polymer core comprises a polymer with low nonspecific binding.

Further provided is a device for handling liquids on an automated chemistry analyzer, said automated chemical analyzer having one or more crane assemblies, comprising (1) a liquid handling probe, e.g., any of the liquid handling probes embodiments described above; (2) a probe mount for securing said liquid handling probe to a crane assembly of the automated chemistry analyzer; and (3) a probe guide attached to said probe mount (e.g., via a probe mounting bracket). In some embodiments, a pliant member is interposed between the probe mount and said probe guide. In some embodiments, the liquid handling probe is affixed to the probe guide. In some embodiments, the device further comprises a collision detection sensor that is operably connected to the pliant member. In some embodiments, the liquid level sensing mechanism is operably connected to the conductive polymer core through the probe guide. In some embodiments, the liquid handling probe comprises a liquid level sensing mechanism operably connected to the conductive polymer core. In some embodiments, the liquid level sensing mechanism is operably connected to the conductive polymer core through the probe guide.

Further provided is a system or method for minimizing collision damage to a liquid handling probe, comprising: a liquid handling probe affixed a probe guide, said probe guide attached to a probe mount with a pliant member interposed between the probe guide and said probe mount, wherein collision between an object and the liquid handling probe results in displacement of the probe guide, and distortion of said pliant member, wherein said distortion of said pliant member reduces force generated between said object and said liquid handling probe during the collision. In some embodiments, distortion of said pliant member activates a collision detection sensor that then generates a signal received by a controller. In some embodiments, the controller alters the trajectory of the liquid handling probe following reception of the signal from the collision detection sensor. In some embodiments, the collision detection sensor has an optical path. In some embodiments, distortion of the pliant member causes an opaque flag to move through the optical path of the collision detection sensor.

DETAILED DESCRIPTION OF THE INVENTION

Figure 1:
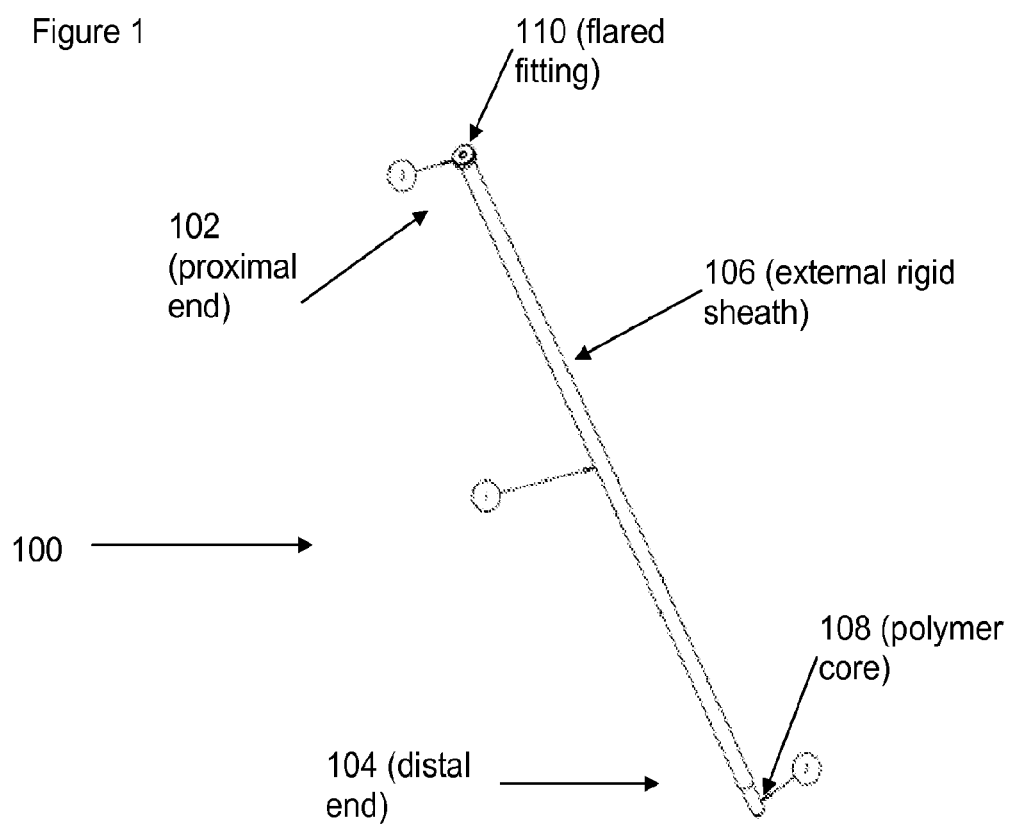
FIG. 1 shows a liquid handling probe 100 of the invention.

Provided herein is a liquid handling probe 100 with a rigid external sheath 106 and a polymer core 108, with reference to FIG. 1. The polymer core 108 can have an internal fluid conduit that facilitates aspiration and delivery of fluids. The use of an external rigid sheath 106 provides a secure point of attachment to a motion system of the analyzer that is used to align the liquid handling probe 100 with a fluid reservoir. Such motion systems include linear gantries, rotary gantries, and articulated arms. The rigidity of the external sheath simplifies alignment of the liquid handling probe 100 by assuring that the relative position between a point of attachment to a motion system and the terminus of the probe that contacts the fluid sample is fixed. This additionally permits the use of system designs that incorporate liquid handling probes of extended length. The external rigid sheath 106 may be made of any suitably rigid material, including rigid plastic or metal. In some embodiments, the external rigid sheath is made of a conductive material. Suitable materials include, but are not limited to stainless steel, steel alloys, aluminum, copper, and copper alloys. The external rigid sheath can serve as a connection for a fluid level sensing circuit, and/or as a connection point between the fluid level sensing circuit and the polymer core 108. The surface of the external rigid sheath can be polished to reduce the impact of accidental immersion in liquid and to ensure good electrical contact. In some embodiments, the external rigid sheath has an electropolished surface.

The polymer core 108 extends from a terminus of the external rigid sheath 106, and serves as the sole fluid contact surface. In some embodiments, the polymer core 108 is made of a material that has minimal interactions with molecules in solution, i.e., a material with low nonspecific binding. This reduces carryover due to nonspecific binding of molecules in a first solution and subsequent undesirable release of the bound molecules into a second solution. Suitable low nonspecific binding materials include, but are not limited to, polypropylene, polyethylene, fluoropolymers, silicone materials, and copolymers.

In some embodiments, the polymer core is made of a conductive or semiconductive polymer. Suitable conductive polymers include, but are not limited to, polypropylene, polyethylene, fluoropolymers, silicone, and copolymers with inclusions of graphite or other conductive materials at a density suitable to support the flow of electric current. In some embodiments, the conductive or semiconductive polymer has a bulk resistance of less than 0.25 Ω*m. In some embodiments, the polymer core is made of a nonconductive material that has been treated to provide it with a conductive or semiconductive coating.

Use of a conductive or semiconductive polymer core 108 allows this portion of the liquid handling probe 100 to serve as a sensing portion of a liquid level sensing circuit. Such fluid sensing circuits, which rely at least in part on contact of conductive material with liquid, are known. In some embodiments, the liquid level sensing circuit incorporates the liquid handling probe 100 as a portion of a capacitor, and can be sensitive to direct contact with liquid and/or conductive surface and proximity to a liquid or conductive surface.

The use of a liquid level sensing circuit permits the system to verify contact with a liquid sample. Accordingly, the system can estimate the volume of the sample based on the position of the liquid handling probe, and adapt to different sample volumes. The use of a liquid level sensing through the polymer core can also permit the system to control the extent to which the liquid handling probe is lowered into the liquid sample, thereby limiting the surface area exposed to the liquid sample and minimizing potential carryover.

Conductive and semiconductive polymers are capable of conducting electric current. Conventional metallic conductors are typically very efficient conductors. In embodiments where the rigid external sheath 106 is conductive, intimate contact between the rigid external sheath 106 and the polymeric core 108 can allow the rigid external sheath 106 to serve as a connecting surface between a liquid level sensing circuit and the polymeric core 108 of the liquid handling probe 100. Intimate contact between the rigid external sheath 106 and the polymeric core 108 can be due to pressure exerted by the external surface of the polymeric core 108 against the inner surface of the rigid external sheath 106, by the use of an adhesive layer placed between the polymer core 108 and the rigid external sheath 106, or a combination of the two. In such applications, the adhesive layer may be conductive or semiconductive.

A less efficient conductive polymeric core 108 limits the length over which it forms an effective sensor. In such cases, the rigid external sheath 106 can extend over the majority of the surface of the liquid handling probe 100 and approach the terminus of the probe. This is in harmony with the function of the rigid external sheath 106 to fix the relative positions between the proximal terminus 102, near where the liquid handling probe 100 is fixed to the motion carriage, and the distal terminus 104, near where the liquid handling probe 100 contacts liquids. The point at which the polymeric core 108 exits the rigid external sheath 106 can act as a surface that can sequester fluid during liquid transfer, thus in some embodiments, this region of the probe is kept away from the liquid surface. Given the present design, one of skill will understand how to balance these opposing needs. In some embodiments the polymeric core 108 extends from about 0.25 to about 3 inches from the distal terminus 104 of the liquid handling probe 100. In some embodiments, the polymeric core 108 extends from about 0.25 to about 0.75 inches from the distal terminus 104 of the liquid handling probe 100. In some embodiments, the polymeric core 108 extends about 0.35 inches from the distal terminus 104 of the liquid handling probe 100.

Use of a liquid level sensing circuit that incorporates the polymer core 108, as described above, also allows the system to detect and correct misalignment of the liquid handling probe 100. As noted above, a liquid level sensing circuit can detect the proximity of conductive surfaces. Input from such a liquid level sensing circuit can be use by the system to halt movement of the liquid handling probe 100 prior to a collision. This advantageously prevents damage to the surface of the liquid handling probe 100, e.g., scratches or chips, that could serve as a fluid reservoir and result in carryover. In some embodiments, the system may utilize known conductive surfaces as reference points, e.g., to calibrate or adjust the position of the motion carriage carrying the liquid handling probe 100. These reference points may be portions of the system that are located for additional purposes, or may be included in the system solely for the purpose of alignment.

In the event of damage to the liquid handling probe despite such precautions, the use of a polymeric core 108 as the fluid contact surface advantageously continues to present a low nonspecific binding polymer surface to the liquid, despite the presence of scratches, chips, and other imperfections. This limits potential carryover to the unintentional transfer of fluid volumes, which can in any event be dealt with using a simple washing method to physically displace any carryover fluid volumes.

In some embodiments, the polymeric core 108 may exit the proximal end 102 of the external rigid sheath 106 to form a connection with other portions of a pipetting assembly, which typically includes a fluid pump. In such applications, the terminus of the polymeric core 108 that connects to the pipetting assembly may be a flared fitting 110. In some embodiments, the flared fitting 110 is simply an expanded portion of the polymeric core 108. This simplifies installation and replacement of the liquid handling probe 100 and advantageously provides a direct connection between pumping portions of the pipetting assembly and the fluid sample.

Figure 2:
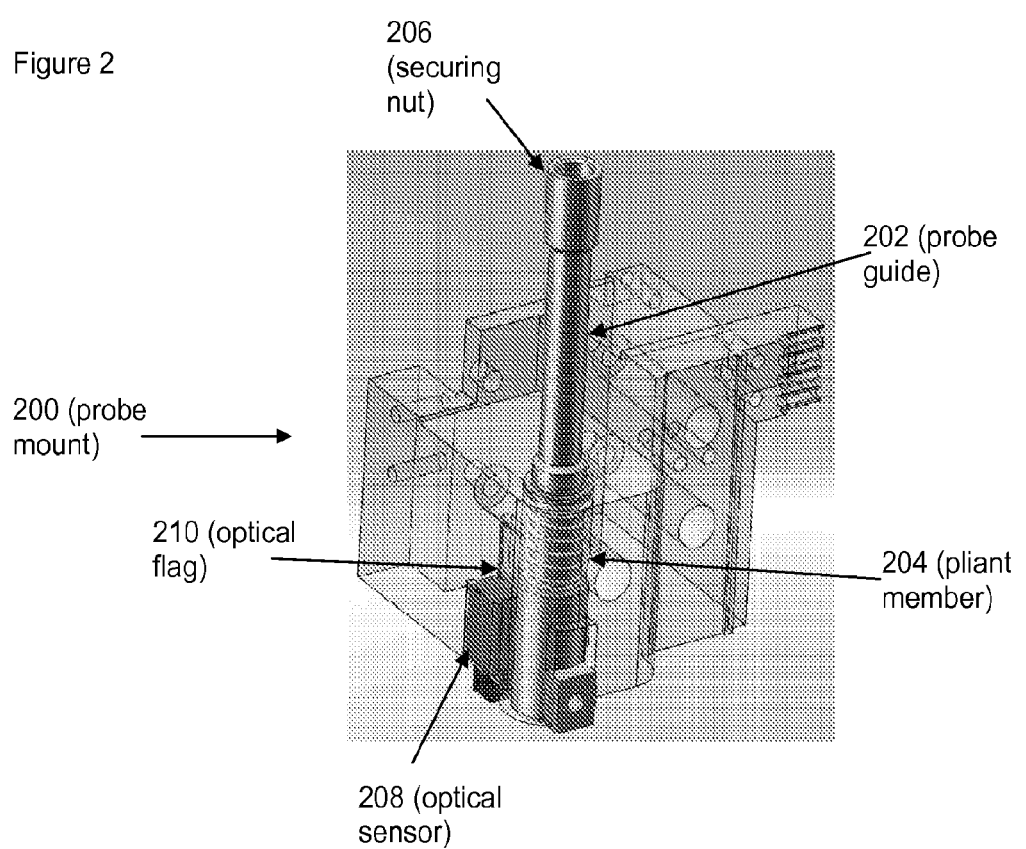
FIG. 2 shows a shock absorbing probe mount 200 of the invention.

Further provided herein is s probe mount 200, e.g., for minimizing damage to liquid handling probes, as exemplified in FIG. 2. The probe mount 200 can be affixed to a transport carriage controlled by the system, and moved to different locations within the system. Transport carriages include, but are not limited to, one, two and three dimensional gantry systems, rotary cranes, articulated arms, and other transports suitable for the geometry of a particular system. In some embodiments, the liquid handling probe 100 can rest vertically within a probe guide 202 that interfaces with the probe mount 200. The probe guide 202 may be any configuration that can securely hold a liquid handling probe. Suitable configurations include hollow cylinders, channels, and shafts with multiple attachment points. In some embodiments, the probe guide 202 is a hollow cylinder. The probe guide 202 may also include a feature that a user can loosen to remove a liquid handling probe 100 or tighten to secure a liquid handling probe 100. In some embodiments, this feature is a nut 206 located at one end of the probe mount 200, In order to minimize damage to a mounted liquid handling probe 100, the probe guide 202 can be free to move within a probe guide channel incorporated into the probe mount 200. This free movement permits a mounted liquid handling probe 100 to move during a collision, minimizing the impact pressures of the collision, hence minimizing damage to the probe. Such damage may be to the surface of the liquid handling probe 100, in the form of scratching or pitting, or may involve bending or crimping of the liquid handling probe 100. The probe guide 202 may be secured at one end of the probe guide 202 channel using a pliant or resilient connection 204. In such an embodiment, the liquid handling probe 100 can be returned to its proper position once a collision is resolved.

In some embodiments, the pliant or resilient connection 204 is a spring.

In some embodiments, the probe mount 200 includes a collision sensor, which detects impacts to the liquid handling probe 100 by detecting movement of the probe guide 202. The system can thus halt further movement of the liquid handling probe 100 when a signal from the collision sensor indicates that the liquid handling probe 100 has made unintended contact. In some embodiments, the system can alter the trajectory of the moving liquid handling probe 100 when a signal from the collision sensor indicates that the liquid handling probe 100 has made unintended (inadvertent) contact. Such an altered trajectory can include reversing the direction of movement. For example, if a liquid handling probe 100 held by a probe mount 200 equipped with a collision sensor encounters a solid object while moving downwards the collision sensor will provide a signal to the system. Subsequently the system may direct the transport carriage to which the probe mount 200 is affixed to halt further movement, thereby minimizing damage to the liquid handling probe 100. In some embodiments, the system can direct the transport carriage to which the probe mount 200 is affixed to move upwards. Intervention by the system can minimize damage to a liquid handling probe 100 by reducing the force and duration of impact. In addition to taking steps to minimize damage to the liquid handling probe 100, the system can notify the user after receiving a signal indicating that a collision has occurred.

There are a number of suitable mechanisms for sensing collision by movement of the probe guide 202, including the use of an optical sensor, Hall effect sensor, or other position-dependent sensor that is operatively connected to the probe guide 202. In some embodiments, the collision sensor is an optical sensor 208 used in combination with a positional flag 210. The positional flag 210 can be mounted on the probe guide 202 and the optical sensor incorporated into the probe mount 200. Alternatively, the optical sensor 208 can be incorporated into the probe guide 202 and the positional flag 210 attached to the probe mount 200.

The probe mount 200 can also serve as a point for connection to a liquid level sensing circuit in instance where the liquid handling probe 100 forms part of the liquid level sensing circuit. In some embodiments, the probe mount 200 provides a fitting for attachment of a conductive portion of a liquid handling probe 100. In some embodiments, the probe guide itself provides a connection to the liquid level sensing circuit. This simplifies attachment or replacement of a liquid handling probe 100 that incorporates liquid level sensing features by integrating the acts of physically attaching the liquid handling probe 100 to the system and making a connection to the liquid level sensing circuit.

In some embodiments, the liquid level sensing circuit can detect proximity to conductive surfaces. In such an embodiment, the liquid level sensing circuit can be used in conjunction with the liquid handling probe as described above to provide a signal to the controller on approach to a solid surface. Such a signal may be used to avoid collision with a solid surface. The signal provided by a liquid level sensing circuit can also be used to detect the presence of alignment features on the system, thereby determining of the position of the liquid handling probe 100 within the system. Determination of the position of the liquid handling probe 100 relative to alignment features on the system may be used for automated alignment of the transport carriage responsible for movement of the liquid handling probe 100. Such alignment features can be located to perform additional functions, or placed on the system specifically for purposes of alignment.

In some embodiments, the invention incorporates the low carryover liquid handling probe 100 described above with the damage-minimizing probe mount 200. The carryover minimizing features of these devices are complementary, and the combination of the two may provide optimal system performance in addition to greatly simplifying the task of installing or replacing the liquid handling probe 100.

While detailed descriptions of one or more embodiments have been give above, various alternatives, modifications, and equivalents will be apparent to those skilled in the art without varying from the spirit of the invention. Moreover, except where clearly inappropriate or otherwise expressly noted, the features, devices, and/or components of different embodiments may be substituted and/or combined. Thus, the above description should not be taken as limiting the scope of the invention. One or more elements of one or more embodiments may be combined with one or more elements of one or more other embodiments without departing from the scope if the invention.

The invention claimed is:

1. A liquid handling probe, comprising:
a) an elongated rigid sheath with a distal terminus;
b) a conductive polymer core that is partially enclosed within said elongated rigid sheath, said conductive polymer core including
an internal fluid conduit and
a conductive polymer tip, said conductive polymer tip comprising a portion of the conductive polymer core that protrudes from the distal terminus of the elongated rigid sheath; and,
c) a liquid level sensing mechanism operably connected to the conductive polymer core, such that the conductive polymer core is the sole liquid contact surface of the liquid handling probe for liquid level sensing,
wherein the elongated rigid sheath is conductive, and the conductive polymer core is in intimate electrical contact with said elongated rigid sheath.

2. The liquid handling probe of claim 1, wherein the conductive polymer core extends beyond the distal end of the elongated rigid sheath at least 0.25 inches.

3. The liquid handling probe of claim 1 wherein the elongated rigid sheath has a proximal terminus, and the conductive polymer core protrudes from said proximal terminus to form a flared fitting.

4. The liquid handling probe of claim 1, wherein the liquid level sensing mechanism is a capacitance based liquid level sensing circuit.

5. The liquid handling probe of claim 1, wherein the conductive polymer core comprises a conductive polymer with a bulk resistivity of less than 0.25 $\Omega$*m.

6. The liquid handling probe of claim 1, wherein the conductive polymer core comprises a conductive fluoropolymer.

7. The liquid handling probe of claim 1, wherein the conductive polymer core comprises a polymer with low nonspecific binding.

8. The liquid handling probe of claim 1, wherein the elongated rigid sheath comprises stainless steel.

9. The liquid handling probe of claim 1, wherein the elongated rigid sheath comprises electropolished stainless steel.

* * * * *